United States Patent [19]
Frigg

[11] Patent Number: 5,653,709
[45] Date of Patent: Aug. 5, 1997

[54] MODULAR MARROW NAIL

[75] Inventor: Robert Frigg, Davos-Platz, Switzerland

[73] Assignee: Synthes (U.S.A.), Paoli, Pa.

[21] Appl. No.: 333,873

[22] Filed: Nov. 3, 1994

Related U.S. Application Data

[63] Continuation of Ser. No. 141,993, Oct. 28, 1993, abandoned.

[30] Foreign Application Priority Data

Dec. 4, 1992 [WO] WIPO ............... PCT/CH92/00235

[51] Int. Cl.⁶ ........................................... A61B 17/72
[52] U.S. Cl. ................................... 606/64; 606/62
[58] Field of Search ........................... 606/62, 64, 63, 606/60, 67, 68

[56] References Cited

U.S. PATENT DOCUMENTS

| | | | |
|---|---|---|---|
| 2,672,861 | 3/1954 | Jonas et al. | 606/63 |
| 3,459,180 | 8/1969 | Ross | 606/67 |
| 5,074,882 | 12/1991 | Grammont et al. | 606/63 |
| 5,263,955 | 11/1993 | Baumgart et al. | 606/63 |
| 5,300,074 | 4/1994 | Frigg . | |

FOREIGN PATENT DOCUMENTS

| | | |
|---|---|---|
| 2084621 | 6/1993 | Canada . |
| 10491138 | 6/1992 | European Pat. Off. . |
| 0550814A2 | 7/1993 | European Pat. Off. . |
| 19115200.3 | 3/1992 | Germany . |

*Primary Examiner*—Guy V. Tucker
*Attorney, Agent, or Firm*—Fish & Richardson P.C.

[57] ABSTRACT

A marrow nail includes a nail 1 having a distal end 2, a proximal end 3, a longitudinal axis 4, and a slot 5 in the area of the proximal end, running transverse to the longitudinal axis 4. A cylindrical casing 10 is provided, which can be slid onto the proximal end 3 of marrow nail 1. This casing 10 exhibits a cylindrical axis 11 as well as at least two openings 12, 13 placed at opposite ends of the cylindrical cover 14. The casing 10 is formed in such a way that upon being slid onto marrow nail 1, it can be brought into an axial fastening position relative to the nail. Openings 12, 13 are thereby positioned in the fastening position of casing 10 in the area of slot 5 and with the latter, marrow nail 1 and casing 10 form a transverse channel 12, 5, 13 to admit bone fixation devices.

13 Claims, 3 Drawing Sheets

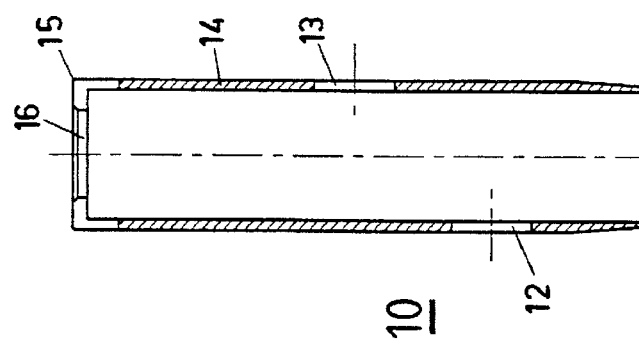
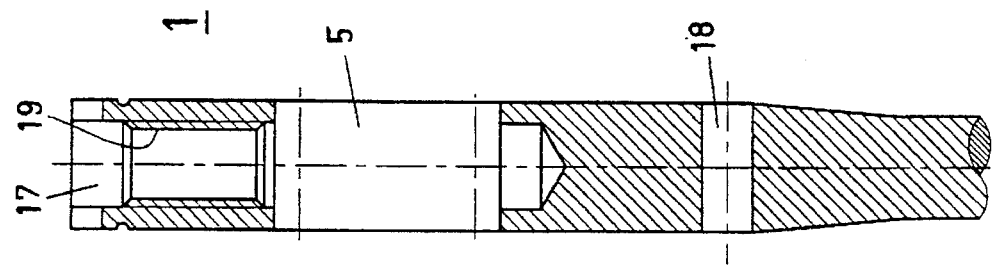
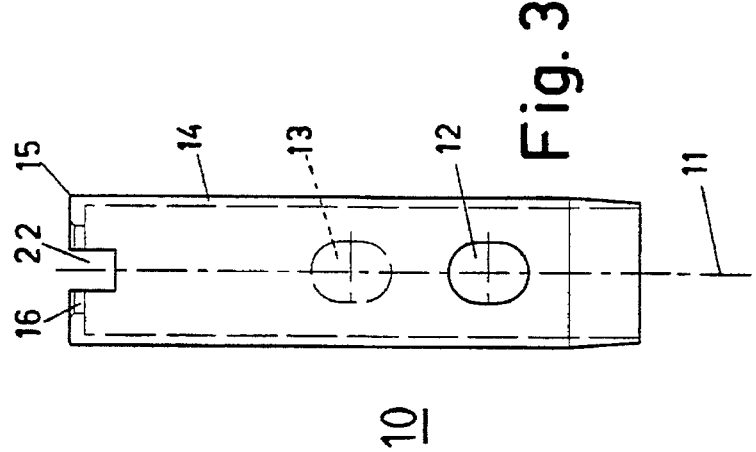
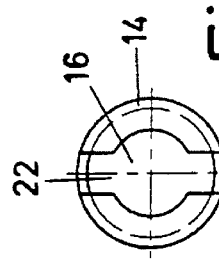
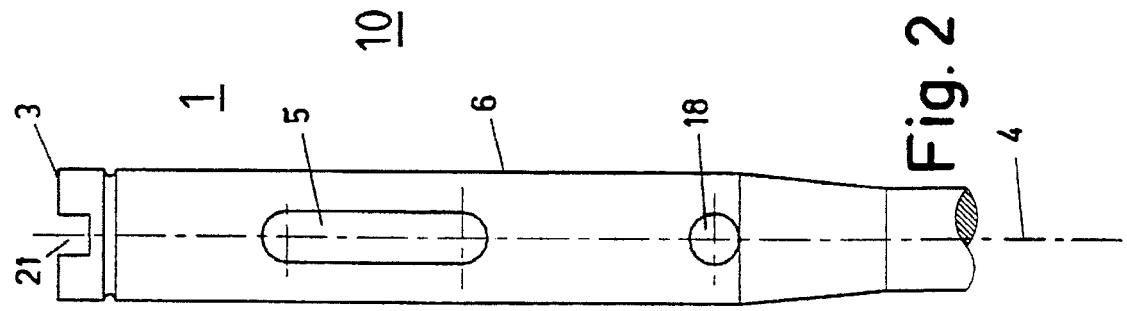

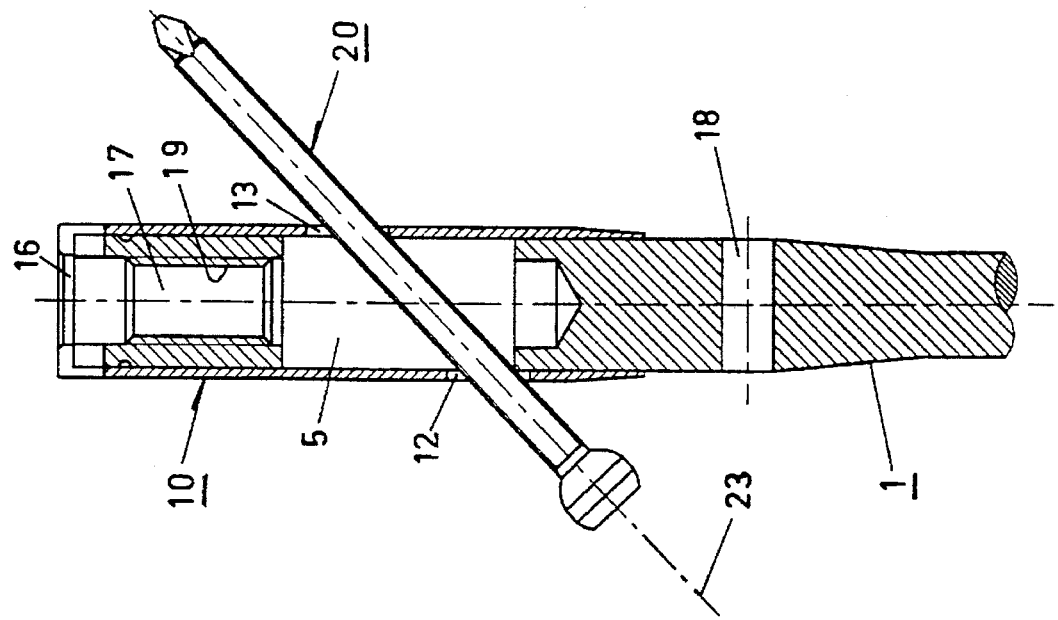
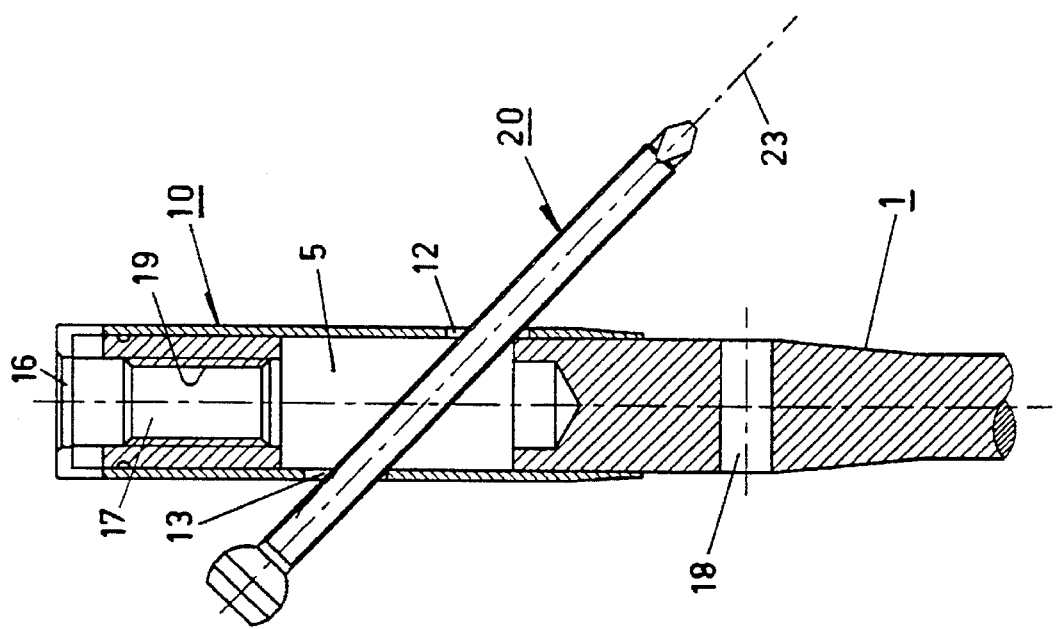

MODULAR MARROW NAIL

This is a continuation of application Ser. No. 08/141,993 filed on Nov. 28,1993, now abandoned.

FIELD OF THE INVENTION

This invention relates to a marrow or intramedullary nail and in particular to a marrow nail which is adaptable to a variety of applications.

BACKGROUND OF THE INVENTION

Marrow nails are load-bearing devices which, using the so-called marrow-nailing technique, effect intramedullar stabilization of bone fractures by mechanical bridging.

Until recently, marrow nails were categorized into conventional marrow nails and locking nails. The considerations which led to this differentiation in this technical specialty, were based on the opinion that in spite of lacking a locking option, conventional marrow nails were the standard marrow nails to be used. This perception has become outdated, and a strong trend exists toward making locking nails the standard. However, within the category of locking nails there is also a trend toward marrow nails that are not hollow as well as marrow nails with various locking options.

The greatest degree of multiplicity is in marrow nails for the femur, with various kinds of locking. The reason for this can be found in the complexity of femur fractures and their treatment. Each type and location of fracture requires an appropriate type and location of locking at the proximal end of the nail.

The various types and positions of proximal locking of femur marrow nails had led to a baffling multiplicity of structural varieties. This is extremely disadvantageous. For one thing, high inventory costs to hospitals are incurred, since all dimensions and types must be stored because the operation must take place immediately after admission of the patient. A multiplicity of various sets must also be prepared, which is another source of great expense. A special problem for small medical facilities, which deal with the majority of the world's patients, are the costs and the complexity of maintaining inventories and instrument sets. This often causes them to switch to other, less elegant methods of dealing with fractures.

A locking nail useful in a variety of situations is disclosed in DE-U1 9115200.3. It is equipped with an axially telescoping but torsionally strong casing, to permit compression and distraction of fragments of fractured hollow bones. The fastening of the telescoping casing relative to the marrow nail is achieved only by passing a bone screw through both parts, so that the position of the opening in the casing relative to the marrow nail's slot is not determined until the last step in the operation. Even after locking is complete, the screw can still be displaced along a relatively wide range of about 35% of the slot.

SUMMARY OF THE INVENTION

The present invention provides a marrow nail assembly which reduces the variety of implants and instruments to a minimum, simplifies the operating technique, and unequivocally defines the relative positions of the nail and its accompanying casing.

A marrow nail assembly according to the invention is distinguished by a modular design which can be adapted to the specific bone fracture at hand. Basically, the marrow nail assembly according to the invention can be used for all applications on the femur and other hollow bones. Specifically, the assembly according to the invention comprises a marrow nail having a distal end, a proximal end, and a longitudinal axis. A slot through the nail is positioned in the area of the proximal end, running transverse to the longitudinal axis. The nail assembly also includes a cylindrical casing which can be slipped onto the proximal end of the nail. The casing has a cylindrical axis and at least two openings situated at opposite sides of its cylindrical wall for receiving bone fixation devices which pass through the openings and through the slot in the nail.

BRIEF DESCRIPTION OF THE DRAWINGS

The invention will be further described with reference to the accompanying drawings which illustrate the invention by reference to a femur marrow nail, it being understood that the invention can be used for other hollow bones with appropriate adjustment to the anatomical conditions.

In the drawings:

FIG. 2 is an enlarged side elevational view of the proximal segment of the marrow nail of FIG. 1.

FIG. 3 is an enlarged side elevational view of the casing of FIG. 1.

FIG. 4 is a top plan view of the casing of FIG. 3.

FIG. 5 is a vertical cross section through the marrow nail of FIG. 2, offset 90°.

FIG. 6 is a vertical cross section through the casing of FIG. 3, offset 90°.

FIG. 7 is a side elevational view, partly in vertical section, of a marrow nail assembly according to the invention in its assembled condition with a bone screw inclined downwardly as a bone fixation device.

FIG. 8 is a side elevational view, partly in vertical section of the marrow nail assembly in its assembled condition with a bone screw inclined upwardly as a bone fixation device.

Figure 1:
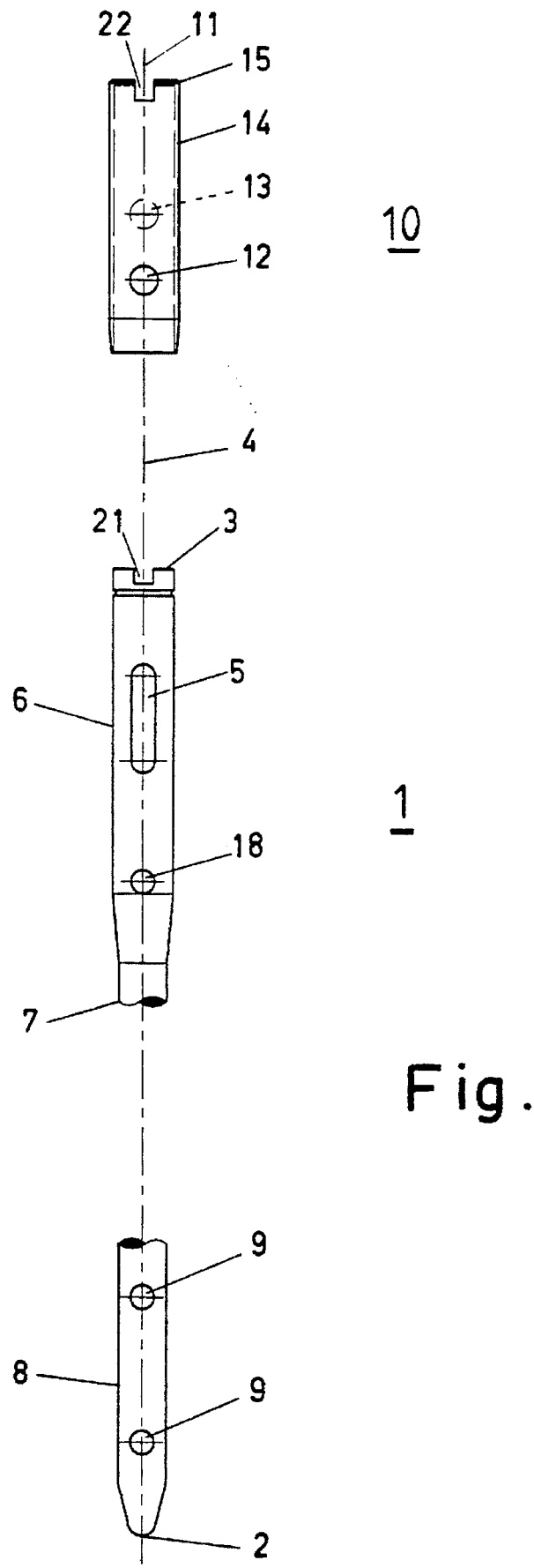
FIG. 1 is a side elevational view of the marrow nail assembly according to the invention in a dismantled condition.

A marrow nail assembly according to the invention in depicted in FIGS. 1 to 8 used as a femur marrow nail. The assembly comprises a nail 1 which essentially consists of a round bar with a solid cross section. It has three different sections arranged serially in the direction of its longitudinal axis 4: a proximal segment 6, a central segment 7 and a distal segment 8, the distal segment having a tip 2. The central and distal segments 7, 8 have diameters such that they can be inserted into the medulla of the femur, without the medulla having to be drilled out. In the distal segment 8, locking holes 9 are located.

The proximal segment 6 has a diameter that is independent of the diameter of the two other segments 7 and 8. It has a transverse slot 5 with a length of 6 to 40 mm, preferably 20 to 30 mm. As shown in FIGS. 7 and 8, through the slot 5 various locking elements 20, such as bone screws or blades, can be passed. A transverse hole 18 below the slot 5 permits insertion of a locking screw which is fixed in position and direction; this, however, is optional and may be omitted.

As shown in FIGS. 2 and 5, the end 3 of the proximal segment 6 has a centrally located socket 17 with interior threading 19 to accommodate instruments (which are not shown) for implanting and extracting the nail 1. The proximal end 3 is also provided with a groove 21, running transverse to the longitudinal axis 4 for aligning the above-mentioned instruments about the longitudinal axis 4.

If the marrow nail according to the invention is used to treat a mid-shaft fracture, it is inserted into the medulla with no modification, i.e. in a completely conventional manner. If there is a subtrochanteric or intratrochanteric fracture, the invention provides, as an additional element of the nail assembly, a casing which is slipped onto the proximal end 3 of the nail.

As shown in FIG. 1 the casing 10 essentially consists of a hollow cylindrical segment having a longitudinal axis 11. The distal end of the casing is open, but the proximal end 15 of casing 10 is closed, except for a central borehole 16, so that in slipping casing 10 onto the marrow nail 1, an axial attachment position is achieved. On opposite sides of the cylindrical wall 14 of the casing 10 are two openings 12, 13. When casing 10 is slipped on the proximal end 3 of marrow nail 1, these openings are positioned opposite to slot 5. This creates a transverse channel through the nail 1 (through slot 5) and through casing 10 (through openings 12, 13), for reception of a bone fixation device 20, which is shown in FIGS. 7 and 8 as a bone screw.

Depending on the type and position of the openings 12, 13 in the cylindrical wall 14 of casing 10, bone fixation devices of various types and sizes can be inserted. Besides the bone screws depicted in FIGS. 7 and 8, so-called bone blades may be used. They are described in more detail in EP-A1 0 491 138, for example, and are particularly well suited to deal with bone fractures close to the joint, especially in the area of proximal and distal femur fractures, as well as on the proximal tibia. In using such a bone blade, openings 12, 13 are preferably configured in elongated form.

With a bone fixation device 20 passed through openings 12, 13 and the slot 5 that lies between them, casing 10 and marrow nail 1 are essentially axially locked with one another. The axial displacement of casing 10 relative to marrow nail 1 should be at most 20%, and preferably at most 10% of the total length of the slot. If, for example, the slot is 25 mm long, the displacement should be less than 5 mm, preferably less than 2.5 mm. However, preference should be given to an axial displacement of 5% at most, preferably 2% at most.

The bone fixation device 20 can be tilted within a wide angular range relative to longitudinal axis 4. The connection line through the centers of the corresponding openings 12, 13 can form an angle of 30° to 150°, preferably of 45° to 135°, with longitudinal axis 4.

Preferably, bone fixation device 20 will not be inserted at a 90° angle, i.e., in other words, openings 12 and 13 are preferably not placed at the same height. It is particularly advantageous if one of the openings 13 is positioned at the proximal end of slot 5, and the other opening 12 lies at the distal end of slot 5, as is depicted in FIGS. 7 and 8. With such an arrangement the above-mentioned displacement of casing 10 and marrow nail 1 after insertion of bone fixation device 20 is virtually reduced to zero.

Casing 10 is provided on its proximal end with a groove 22 transverse to its longitudinal axis 11. The groove 22 possesses the same dimension as the groove 21 on the proximal end 3 of marrow nail 1. Suitable implantation and extraction instruments (not shown), for example, using sliding blocks, can be configured to lock into groove 22 of casing 10 and into groove 21 of nail 1, thus coordinating these two parts 1, 10 with each other and locking them rotationally. By means of a central screw (not shown), implantation and extraction instruments can be used which are screwed into the bore hole 16 in casing 10 and socket 17 of marrow nail 1, and locked into position. This screwing engagement simultaneously locks casing 10 on the proximal end 3 of the nail. With the firmly screwed-in instrument set, marrow nail 1 can be driven into the marrow space. Depending on the configuration of openings 12, 13 of casing 10, an appropriate sighting mechanism can be mounted on the implantation instrument. By means of such a sighting mechanism, the proximal bone fixation devices 20 can be guided through openings 12, 13 and inserted through the slot 5 of marrow nail 1.

The combination of marrow nail 1 and casing 10 according to the invention simplifies the adaptation of the implant to the actual fracture to be taken care of. For the clinician this means that be can deal with all femur shaft fractures, and a very wide variety of proximal femur fractures by using a single type of marrow nail. The only thing which he needs in addition to deal with special indications (i.e., in about 10% of all cases) is a casing 10 that is appropriate to the fracture. These casings 10 are not dependent on the length or diameter of the marrow nail 1. An inventory of approximately five different casings can thus replace an inventory of about 200 different conventional marrow nails (5 different marrow nail types, with about 4 different diameters and about 10 different lengths).

The number of conventional implants is actually somewhat higher, since with certain systems of marrow nails, right and left configurational types exist. This doubling of implants is not necessary with the system according to the invention, since casing 10 simply has to be turned 180°, as is depicted in FIGS. 7 and 8.

A similar reduction in number applies to the instruments, for apart from the various sighting attachments, no indication-specific instruments are needed for the system according to the invention.

The casing 10 slid onto marrow nail 1 is attached by the bone fixation device 20 itself, i.e. bone fixation device 20 fixes casing 10 in rotation and axial displacement distally. Possible axial displacement of casing 10 proximally can be prevented by screwing casing 10 to the nail. Thus a screw (not shown) may be inserted through borehole 16 on the proximal end 15 of casing 10 into the internal threading 19 of borehole 17 located on the proximal end 3 of the nail, and turned tight. Such safeguard, however, is not absolutely necessary, since the femur is exclusively subject to axial compression forces.

If the bone fixation device 20 must be secured against displacement along its axis 23 or against rotation, this again can be done by insertion and tightening of a screw (not shown) through the proximal end 15 of borehole 16 in casing 10 into borehole 17 with internal threading 19 on the proximal end 3 of the nail, to engage bone fixation device 20.

The usual implant materials for osteosynthesis are applicable as materials for the marrow nails according to the invention.

What is claimed is:

1. A marrow nail assembly comprising an integrally formed nail having a proximal section, a distal section of reduced diameter relative to said proximal section, a longitudinal axis, and a transverse slot having a cross section elongated in the direction of said axis, in combination with a cylindrical casing fitted over the proximal section of the nail only, said casing having a length not greater than said proximal section, a cylindrical wall and a single pair of openings in said wall on opposite sides of said casing, each of said openings being elongated in configuration in the direction of said axis and being located to form, with the transverse slot in the nail, a transverse channel through the casing and nail for receiving bone fixation devices, wherein a line through the centers of the openings in the casing forms an angle of from 30° to 150°, other than 90°, with the longitudinal axis of the nail when the casing is fitted over the proximal section of the nail, the position of said openings relative to said slot being such as to secure relative axial fixation of said casing and nail by a bone fixation device seated in said channel.

2. The marrow nail assembly according to claim 1 wherein the casing is closed at its proximal end.

3. The marrow nail assembly according to claim 1 wherein the openings in the casing are so positioned that when a bone fixation device is inserted into the transverse channel, axial displacement of the casing with respect to the nail is at most 20% of the total length of the slot.

4. The marrow nail assembly according to claim 3 wherein the axial displacement is at most 10% of the total length of the slot.

5. The marrow nail assembly according to claim 4 wherein the axial displacement is at most 5% of the total length of the slot.

6. The marrow nail assembly according to claim 5 wherein the axial displacement is at most 2% of the total length of the slot.

7. The marrow nail assembly according to claim 1 wherein the cylindrical casing at its proximal end has a cylindrical borehole.

8. The marrow nail assembly according to claim 1 wherein the marrow nail at its proximal end has a central socket.

9. The marrow nail assembly claimed in claim 8 wherein the socket is threaded.

10. The marrow nail assembly according to claim 1 wherein marrow nail and casing are configured to be able to be turned against each other.

11. The marrow nail assembly according to claim 1 wherein the openings are in the form of slots to admit a bone blade.

12. The marrow nail assembly according to claim 1 wherein the marrow nail at its proximal end has a groove transverse to its longitudinal axis.

13. The marrow nail assembly according to claim 12 wherein the casing at its proximal end has a groove that corresponds with the groove of the marrow nail.

* * * * *

UNITED STATES PATENT AND TRADEMARK OFFICE
CERTIFICATE OF CORRECTION

PATENT NO.  : 5,653,709

DATED       : August 5, 1997

INVENTOR(S) : Robert Frigg

It is certified that error appears in the above-identified patent and that said Letters Patent is hereby corrected as shown below:

Col. 2, line 41, "in" should be --is--.

Signed and Sealed this

Twenty-eighth Day of April, 1998

Attest:

BRUCE LEHMAN

*Attesting Officer*  *Commissioner of Patents and Trademarks*